United States Patent
Speck et al.

(10) Patent No.: US 9,974,888 B2
(45) Date of Patent: *May 22, 2018

(54) FORMULATIONS FOR DRUG-COATED MEDICAL DEVICES

(75) Inventors: Ulrich Speck, Berlin (DE); Madeleine Caroline Berg, Berlin (DE)

(73) Assignee: INNORA GmbH (DE)

( * ) Notice: Subject to any disclaimer, the term of this patent is extended or adjusted under 35 U.S.C. 154(b) by 1101 days.

This patent is subject to a terminal disclaimer.

(21) Appl. No.: 13/641,941

(22) PCT Filed: Nov. 3, 2010

(86) PCT No.: PCT/EP2010/066751
§ 371 (c)(1),
(2), (4) Date: Oct. 18, 2012

(87) PCT Pub. No.: WO2011/131258
PCT Pub. Date: Oct. 27, 2011

(65) Prior Publication Data
US 2013/0046237 A1    Feb. 21, 2013

(30) Foreign Application Priority Data
Apr. 19, 2010 (EP) .................................. 10160349

(51) Int. Cl.
A61F 2/00    (2006.01)
A61L 29/16   (2006.01)
A61L 31/16   (2006.01)

(52) U.S. Cl.
CPC ............... *A61L 29/16* (2013.01); *A61L 31/16* (2013.01); *A61L 2300/416* (2013.01)

(58) Field of Classification Search
None
See application file for complete search history.

(56) References Cited

U.S. PATENT DOCUMENTS

| | | | |
|---|---|---|---|
| 9,011,896 B2 * | 4/2015 | Speck et al. | 424/423 |
| 9,072,812 B2 * | 7/2015 | Speck | A61L 29/16 |
| 9,078,951 B2 * | 7/2015 | Speck | A61L 29/16 |
| 9,101,684 B2 * | 8/2015 | Speck | A61L 29/16 |
| 9,173,977 B2 * | 11/2015 | Speck | A61L 29/16 |
| 9,629,942 B2 * | 4/2017 | Speck | A61L 29/16 |
| 2010/0209472 A1 * | 8/2010 | Wang | 424/423 |

* cited by examiner

*Primary Examiner* — Hasan Ahmed
(74) *Attorney, Agent, or Firm* — Wood, Phillips, Katz, Clark & Mortimer

(57) ABSTRACT

The present invention is related to a medical device carrying at least on a portion of its surface at least one oxidation-insensitive drug or oxidation-insensitive polymer-free drug preparation and at least one lipophilic antioxidant at a ratio of 3-100% by weight of the at least one antioxidant in relation to 100% by weight of the drug, wherein the at least one oxidation-insensitive drug is selected of taxanes, thalidomide, statins, corticoids and lipophilic derivatives of corticoids, and the at least one lipophilic antioxidant is selected of nordihydroguaiarectic acid, resveratrol and propyl gallate, and wherein scoring or cutting balloons as medical devices are excluded.

10 Claims, No Drawings

FORMULATIONS FOR DRUG-COATED MEDICAL DEVICES

FIELD OF THE INVENTION

The invention relates to the transfer of a drug loosely adhering to the surface of a medical device to a site inside the body, usually in a diseased blood vessel. The most frequent application is local drug therapy during percutaneous transluminal angioplasty (PTA) or percutaneous transluminal coronary angioplasty (PTCA). These interventions are performed to restore blood flow in stenotic or occluded blood vessels, usually in arteries. A catheter is introduced into a major artery. At the distal end the catheter carries a cylindrical balloon in folded state with very small diameter. In this state the balloon can enter or pass the stenotic or occluded segment of the blood vessel. Once positioned in the narrowed segment, the balloon is inflated with low or high pressure to enlarge the lumen of the blood vessel to its original diameter. Simultaneously, a drug may be transferred to the vessel wall to prevent early and late re-narrowing due to hyperproliferation of the injured vessel wall.

BACKGROUND

Medical devices may contain drugs either to improve the tolerance, efficacy or in vivo life-time of the device or the device serves as carrier for the drug. In any case the dose density (e.g. mg drug/mg device or mg drug/mm$^2$ device surface), chemical stability, adherence, release rate, and total amount released are important and frequently critical features of the drug formulation. These properties are the more critical the more the requirements during production and application of the device vary or may even be contradictory. Drug-coated angioplasty catheters are typical examples: the drug coating must adhere firmly to tolerate mechanical stress during production including folding of balloons, crimping of stents, packaging, transportation to customers, and during final application, which involves passage through a narrow hemostatic valve, an introductory sheath or guiding catheter and a variable distance through possibly tortuous and narrow blood vessels. When the balloon is inflated the drug should be released within a minute or less as rapidly and as completely as possible. The problem was demonstrated by Cremers et al. (Cremers B, Biedermann M, Mahnkopf D, Böhm M, Scheller B. Comparison of two different paclitaxel-coated balloon catheters in the porcine coronary restenosis model. Clin Res Cardiol 2009; 98:325-330) who retrieved as much as 50% of the dose from balloons after expansion for one minute in coronary arteries of pigs, whereas other catheters coated with the same drug and dose but in a different formulation released more than 95%. Almost perfect results (i.e., loss of only 10% of dose and residual drug on the balloon after expansion in an artery of about 10%) were achieved with a rigid prototype balloon (Scheller B, Speck U, Abramjuk C, Bernhardt U, Böhm M, Nickenig G. Paclitaxel balloon coating—a novel method for prevention and therapy of restenosis. Circulation 2004; 110: 810-814). The application of the same coating composition to more flexible modern balloon catheters resulted in problems, i.e., larger premature loss of the drug.

Prior Art: Protection from Premature Drug Release

Premature release of a drug from a balloon is a major problem which has been addressed by a variety of methods. Some of them are mechanical, e.g. the use of protection tubes, sleeves, envelops. Examples are U.S. Pat. No. 5,370,614, U.S. Pat. No. 6,306,166, and U.S. Pat. No. 6,616,650 disclosing various protective sheaths which are retracted before the balloon is inflated, or U.S. Pat. No. 6,419,692 proposing a cover which bursts during balloon expansion. A different approach is taken in U.S. Pat. No. 5,893,840 disclosing structured balloon membranes with tiny cavities, WO 94/23787 with roughened balloon membranes to enhance the adherence of coating, or more recently U.S. Pat. No. 7,108,684 proposing a pouch which protects the drug-containing layer on the balloon and WO 2009/066330 disclosing methods placing the drug selectively under the folds of a folded balloon. Although efficacious these methods have the disadvantage of increasing the complexity and cost of production or make handling of the devices more difficult or add to the diameter of the devices (which must be kept as small as possible to facilitate passage through stenotic lesions). In some embodiments the protective membranes or perforated membranes prevent a homogeneous transfer of the drug to the tissue or even put the patient at risks.

Other approaches use either physical or chemical methods to control the release of drugs from a balloon surface, e.g. U.S. Pat. No. 5,304,121 describes a hydrogel which releases the drug only after exposure to a triggering agent; U.S. Pat. No. 5,199,951 relies on thermal activation; according to U.S. Pat. No. 7,445,792 a lipophilic 'hydration inhibitor' protects water-soluble drugs from premature release; and according to U.S. Pat. No. 5,370,614 a viscous matrix protects the drug from premature release, however, the viscous matrix must be protected by a sheath during the passage to the stenotic vessel segment. None of the methods has been tested in practice and proven to fulfill the requirements for fast, reliable and complete drug transfer to the target tissue.

Numerous methods of sustained drug release are known and successfully used in practice but are not applicable to medical devices which are in contact with the target tissue only a few seconds or minutes. Sustained drug release is usually achieved by embedding the drug in a polymer which restricts the diffusion rate to the surface and in this way controls the transfer into the adjacent tissue.

Therefore, a need remains for a method or formulation which protects the coating from premature losses during production, handling, and on the way to the lesion and still allows the immediate and complete release of the active ingredient at a location and point in time determined by the user.

An advantageous way to control adherence and release of a drug from a medical device, e.g., an angioplasty balloon, is the selection of a suitable formulation and coating which do not require mechanical protection, or additional physical or chemical interaction with the coating except the usual operation of the device, e.g., inflation of a folded balloon to induce the release of the drug. Although desirable and frequently tried, the conflicting objectives of perfect adherence before use and immediate release at the site of action make it a difficult task. A large variety of patent applications vaguely disclose measures, compositions and devices to solve this problem either by the selection of drugs, the choice of specific coating processes or formulations containing various additives. Long lists of compounds have been copied from textbooks of chemistry, pharmacology, or pharmacy but even with extensive experimentation disclosures are not sufficiently clear to allow a person familiar with the subject and skilled in the art to come to a satisfactory solution without an inventive step. Examples of prior art are US 2008/0118544 reciting an excessive number of substances and substance classes or U.S. Pat. No. 7,445,795 which discloses the use of 'hydration inhibitors' not applicable to the preferred class of very lipophilic drugs which require 'hydration enhancers' or 'dispersion and dissolution enhancers' as e.g. disclosed in WO 2004/028582. Although the hydrophilic additives (which may be regarded as 'hydration enhancers') work quite well on certain balloon membranes (Scheller B, Speck U, Abramjuk C, Bernhardt U, Böhm M, Nickenig G. Paclitaxel balloon coating—a novel method for prevention and therapy of restenosis. Circulation 2004; 110: 810-814) the adherence of the drug admixed to these excipients to various modern PTA or PTCA balloons is either too weak or too tight resulting in premature loss of a major proportion of the drug or incomplete release at the target site.

Prior Art: Antioxidants

In theory, antioxidants address an almost universal feature of diseased tissue, namely the 'reactive oxygen species', and should have widespread medical applications. In practice, only very few controlled clinical trials have shown beneficial effects of antioxidants (Suzuki K. Antioxidants for therapeutic use: Why are only a few drugs in clinical use? Advanced Drug Delivery Reviews 2009; 61:287-289). Antioxidants are mentioned as potentially useful drugs for the treatment of focal vascular disease such as stenosis, restenosis, atherosclerotic plaques, and vulnerable plaques in US 2009/0136560 with no additive, in U.S. Pat. No. 5,571,523 as agents inducing apoptosis in vascular smooth muscle cells, in WO 2004/022124 either as active drugs or as 'hydration inhibitors'. In US 2008/0241215 probucol, a drug approved for the treatment of hyperlipidemia, a known risk factor for atherosclerosis, is proposed as the active ingredient in stent coating, either alone or combined with rapamycin or another anti-restenotic agent in a slow-release formulation. U.S. Pat. No. 6,211,247 claims pharmaceutical compositions containing an effective dose of resveratrol for preventing or treating various vascular pathologies following coronary interventions. Similarly, US 2007/0037739 discloses local delivery systems comprising various bioactive agents including resveratrol which either alone or in the specified combinations are suitable for treating or preventing abnormal luminal cell proliferation. None of the above-mentioned documents contains data encouraging the use as additives to a lipophilic drug to delay the release rate of the drug and no specific compositions are disclosed which address the above-mentioned problems of adhesion of a drug before the target lesion is reached and immediate release when required.

Small proportions of antioxidants are commonly used to protect drugs or nutrients from decomposition by oxygen or oxidation, an application which has also been proposed for drugs coated on implantable medical devices such as stents (US 2007/0020380, US 2009/0246253) or balloon catheters (US 2005/0037048, US 2009/0246252, especially paragraph [105]). However, antioxidants are commonly used in proportions of less than 1% by weight in relation to 100% by weight of the drug. Normally it is intended to use as less antioxidant as possible, i.e., less than 0.1% by weight in relation to 100% by weight of the drug (Voigt R. Lehrbuch der pharmazeutischen Technologie. 5. Edition, Verlag Chemie, Weinheim-Deerfield Beach, Fla.-Basel, 1984). US 2005/0037048 discloses a specific example which refers to a selected drug in a polymeric matrix requiring an unusually high proportion of antioxidants.

Again, none of the above mentioned documents provides any hint to an advantage in using antioxidants in combination with stable (i.e. oxidation-resistant drugs) and/or at dose levels which provide no therapeutic or prophylactic action.

PRESENT INVENTION

The problem underlying the present invention was the provision of a medical device with an improved adherence of the drug without negative effect on the release of the drug at the target site.

The problem was solved by a medical device according to claim 1. In other words, the problem was solved by a medical device carrying at least on a portion of its surface at least one oxidation-insensitive drug or oxidation-insensitive polymer-free drug preparation and at least one lipophilic antioxidant at a ratio of 3-100% by weight of the at least one antioxidant in relation to 100% by weight of the drug, wherein the at least one oxidation-insensitive drug is selected of taxanes, thalidomide, statins, corticoids and lipophilic derivatives of corticoids, and the at least one lipophilic antioxidant is selected of nordihydroguaiaretic acid, resveratrol and propyl gallate, and wherein scoring or cutting balloons as medical devices are excluded. "Polymer-free" means that no additional polymer is part of the coating. Preferred embodiments are disclosed in the dependant claims. Usually, antioxidants are used to stabilize oxidation-sensitive drugs against degradation by oxygen. They are considered useless in this regard if the drug is stable against oxidative degradation, i.e. if the drug is oxidation-insensitive. Below, the terms "oxidation-insensitive drug", "active drug" and "drug" are used interchangeable all meaning an oxidation-insensitive drug if the invention is concerned.

During testing of a large variety of coating methods, additives and drug combinations the surprising discovery was made that certain lipophilic antioxidants added to less or even more lipophilic and more or less water-soluble drugs, which are oxidation-insensitive, such as inhibitors of cell proliferation or inhibitors of the formation of neovasculature in a defined mass ratio significantly increase the adherence of the drug to a variety of state-of-the art balloon membranes during handling and on the way to the target lesion even if the target lesion is located far away from the site where the device first enters a blood-filled introductory sheath, guiding catheter or vessel containing rapidly flowing blood. Thus, at least one lipophilic antioxidant in an amount of 3-100% by weight is used as an adherence improver for drugs coated on a medical device during this initial step of introducing the medical device into the vasculature. The wording "at least one lipophilic antioxidant" includes single antioxidants but also mixtures of different antioxidants. Other substances or pharmaceutical compounds may be added to further adjust the properties of the product to the demand in respect of stability or other pharmaceutical requirements and tolerance etc.

Scoring or cutting balloon catheters are explicitly excluded as medical devices.

Examples of active drugs are inhibitors of cell proliferation such as taxanes, preferably paclitaxel, docetaxel and protaxel. Alternatively, specific inhibitors of neovascularization such as thalidomide, statins like atorvastatin, cerivastatin, fluvastatin or anti-inflammatory drugs like corticoids or even more preferred lipophilic derivatives of corticoids such as betamethasone diproprionate or dexamethasone-21-palmitate are examples of oxidation-insensitive drugs. Various drugs may be applied or combined if different pharmacological actions are required or efficacy or tolerance is to be improved. Thus, the wording "at least one drug or drug preparation" means that single drugs but also mixtures of different drugs are included. Preferred drugs are either lipophilic (partition coefficient between n-butanol and water >10, or display very poor water solubility (<1 mg/ml, 20° C.). Preferred are those drugs which in dry state are chemically stable during long-term storage without the addition of an antioxidant, e.g., paclitaxel and other taxanes, statins, thalidomide, corticosteroids and lipophilic derivatives of corticoids. Thereof, the preferred ones are paclitaxel, protaxel and docetaxel with paclitaxel being the most preferred drug. Drugs must be used in a dose range providing the desired effect without compromising the technical features of the coated balloon such as flexibility. A preferred dose range is between 1 and 10 µg/mm$^2$ balloon surface, most preferred up to 6 µg/mm$^2$.

The lipophilic antioxidants are solid at temperatures up to 40° C. Preferred are nordihydroguaiaretic acid, propyl gallate or resveratrol, more preferred nordihydroguaiaretic acid or resveratrol, most preferred resveratrol. Probucol is not a preferred additive. As explained above, the wording "at least one drug or drug preparation" means single drugs but also mixtures of different drugs and the wording "at least one lipophilic antioxidant" includes single antioxidants but also mixtures of different antioxidants.

Combinations of these antioxidants with the above-mentioned drugs showed an improved adherence. Different combinations, especially with other oxidation-insensitive drugs, did not show a significantly improved adherence or required very high amounts of the antioxidant which impairs the mechanical features of the balloons (much more than 100% by weight in relation to 100% by weight of the drug).

Lipophilic antioxidant means that the partition coefficient of the antioxidant between n-butanol and water is >1, more preferred >10 and even more preferred >100.

Preferably, the drug is more lipophilic than the antioxidant, i.e., the partition coefficient between n-butanol and water of the drug is higher than the partition coefficient between n-butanol and water of the antioxidant. If, however, an excipient prevents premature loss of the drug from the medical device and/or enhances the fast and complete transfer to the tissue it shall not be excluded because of its physicochemical properties.

At the dose density used the chosen antioxidants do not display relevant therapeutic or prophylactic effects in respect of the disease which is treated by the coated medical device nor is the relative amount of the antioxidant chosen to protect the drug from oxidative decomposition. This means that a non-bioactive dose of the antioxidant is preferred. The dose density and the mass relation of the antioxidant to the drug are solely optimized in respect of adherence of the drug to and release from the medical device surface. The antioxidant dose on the medical device is too low to provide the desired pharmacological effect, i.e., it is ineffective on its own. The antioxidant on the medical device is not required to protect the active drug (e.g., the antiproliferative or immunosuppressive drug) from oxidative decomposition during production, sterilization and storage; at least it is not required at the dose or concentration applied according to this invention. 'Not required' means that the active drug is stable enough without the antioxidant or at an antioxidant dose or dose density or ratio to the active drug below the dose according to the present invention. 'Sufficient stability' means that less than 5% of the active drug is lost due to oxidative decomposition between the coating of the device and the use in patients one year after production if stored at ambient temperature (=drug or drug preparation stable against oxidative decomposition, air-oxygen exposure not excluded). In conclusion the invention relates to a combination of an antioxidant with a drug which needs no protection from oxidative decomposition or at least a dose of the antioxidant which surpasses the amount of antioxidant required protecting the drug from oxidation by its antioxidant action. The antioxidant serves as additive or excipient not functioning as a stabilizer for an oxidation-sensitive biologically active ingredient (drug) nor displaying a therapeutic or prophylactic effect on its own at the selected dose.

The dose of the antioxidant on the surface of a medical device may be defined in respect of the therapeutic drug. Preferred relationships (weight/weight) are 3-100% antioxidant of the weight of the drug. For example, if the dose density of the drug is 5 µg/mm$^2$ device surface, the amount of antioxidant is 0.15-5.0 µg/mm$^2$. Higher proportions of the antioxidant may be selected if either the drug is applied at a dose below 3 µg/mm$^2$ device surface or the adherence of the drug to the device surface is further improved. The antioxidant load of the device may reach 10 µg/mm$^2$. A higher load is possible. Other preferred ranges for the relationship of antioxidant to drug on a weight/weight basis are 5-100%, more preferred 10-100%, and even more preferred 20-100% and most preferred 50-100% in relation to 100% of the drug. Especially the range of 50-100% on a weight/weight basis enhances the adherence significantly. Lower amounts improve the adherence correspondingly less, i.e. the more antioxidant the better is the adherence showing a correlation in the preferred range. However, more than 50% improve the adherence more than would be expected considering a linear correlation. The relationship may also be defined in respect of moles: in a preferred embodiment the antioxidant is present from 10 mole % relative to the drug to 200 mole %. Higher amounts of the antioxidant may be useful; they may be only excluded if they display on their own significant pharmacological prophylactic or therapeutic effects in respect of the disease to be treated.

If more than one drug is used the total weight of the drugs or the total moles of the drugs serve as basis for the calculation of the amount of the antioxidant. If more than one antioxidant is used the total weight of the antioxidants or the total moles of the antioxidants serve as basis for the calculation of the amount of the antioxidants.

Other well tolerated and approved additives and/or excipients may be applied to further improve the mechanical or pharmaceutical properties of the coating. Polymer-free coating compositions are preferred. It is a special advantage of the present compositions that they do not require the use of polymers to prevent premature release of the drug. Nevertheless, small amounts of pharmaceutically acceptable polymers such as polyacrylic acids may be added, e.g., to improve the distribution of the drug on the balloon or adherence of the dry coating during handling. Small amounts mean about 1-20% by weight in relation to 100% by weight of the drug(s). If polymers are used substances with low to moderate molecular weight, i.e., 2000 to 50 000 D are preferred.

Usually, drugs and mixtures of drugs with additives are coated on medical devices as liquid formulations in volatile solvents, according to the current invention preferably without addition of a polymer, i.e. polymer-free. The choice of solvent is important for the structure of the coating in dry state and the adherence and release of the drug from the surface. Preferred organic solvents are acetone, tetrahydrofuran, and various alcohols such as methanol, ethanol, and isopropyl alcohol (isopropanol). Usually, 1 to 30% (volume/volume) water is added. The drug or drugs and the antioxidant may be applied at the same time dissolved in the same solvent or mixture of solvents. Alternatively, they may be separately dissolved in the same or different solvents and sequentially applied. The solution(s) is/are polymer-free in either case. In a preferred embodiment, the medical device has been polymer-free coated with at least one oxidation-insensitive drug and at least one lipophilic antioxidant both dissolved in tetrahydrofuran or a mixture of solvents containing more than 25% (v/v) tetrahydrofuran or each separately dissolved optionally selecting a different solvent for the at least one lipophilic antioxidant. Another preferred embodiment is based on a medical device, which has been polymer-free coated with at least one oxidation-insensitive drug and at least one lipophilic antioxidant both together dissolved in acetone or a mixture of solvents containing more than 25% (v/v) acetone or each separately dissolved optionally selecting a different solvent for the at least one lipophilic antioxidant. Yet another preferred embodiment is a medical device, which has been coated with at least one drug and at least one lipophilic antioxidant both together dissolved in isopropanol or a mixture of solvents containing more than 25% (v/v) isopropanol or each separately dissolved optionally selecting a different solvent for the at least one lipophilic antioxidant. Coating with dry particles such as micro- or nanoparticles, crystals, capsules etc. or particles suspended in a liquid preparation is possible. Coating with particles may be facilitated by a roughened or sticky surface of the medical device.

A variety of coating procedures providing more or less uniform layers on medical devices are known from the literature and are disclosed in patent applications. These include simple dipping, spraying, and methods providing precise doses and homogeneous distributions (e.g., WO 2009/018816). Coating may be applied stepwise, either as multiple layers of the same composition or as layers with different compositions e.g. the drug first and the antioxidant second or in the opposite order. All these methods may be applied to the formulations of the current invention. The sequential coating with, e.g., (a) the drug first and (b) second the antioxidant dissolved in a solvent in which the drug is poorly soluble by, e.g., spraying results in substantially separate layers. This is completely different from the application of antioxidants for chemical protection of oxidation sensitive drugs which requires a homogeneous mixing of the antioxidant with the drug. Thus, a preferred embodiment is a medical device, which has been sequentially coated polymer-free with at least one oxidation-insensitive drug and at least one lipophilic antioxidant in a way that the drug and the antioxidant are not homogeneously mixed.

Furthermore, coated medical devices may be dried under different conditions such as temperature, air flow, gas composition, and pressure at different stages of the production process. They may be stored in water-vapor-tight seals with a separately packed water-absorbing agent within the seal.

Preferred medical devices are balloon catheters, e.g., catheters for angioplasty or coronary angioplasty except scoring or cutting balloon catheters. Most preferred medical devices are balloon catheters for short-lasting use during an interventional image guided therapy. Short lasting use means that the device is not implanted but eliminated from the body when the procedure is finished, usually within less than 10 minutes, but never later than a few, preferably 5, hours after the end of the procedure. Catheters may contain balloon membranes made from various polymers and copolymers, polyamides (nylon 12, pebax), polyethylenes, polyurethanes, various polyvinyls and the like. Independently of the type of material, the adherence and release properties of drugs are improved by the addition of lipophilic antioxidants.

The medical device carries the at least one drug or drug preparation and the at least one lipophilic antioxidant at least on a portion of its surface which is aimed at coming into close contact with the tissue to be treated, e.g., a balloon at the distal portion of a catheter shaft. This means that at least 5%, preferably more than 50%, most preferably more than 90% of the surface is coated. Preferably, the coating is present at least on the surface of the device where it has the widest diameter. If less than 100% of the device's surface is coated, preferably the parts starting with the lowest device diameter are omitted. However, parts such as holds/handles or shafts are omitted per se. A balloon as part of a balloon catheter, which is a preferred medical device, has a central cylindrical part and two opposite conical ends. If less than 100% of the balloon catheter's surface is coated, it is preferred that the cylindrical part is coated and that at least parts of or the complete conical ends remain uncoated.

Another embodiment is a medical device carrying at least on a portion of its surface polymer-free at least one Limus drug or Limus drug preparation and at least one lipophilic antioxidant, which is nordihydroguaiarectic acid or resveratrol, preferably resveratrol, at a ratio of 3-100% by weight of the at least one antioxidant in relation to 100% by weight of the drug, wherein scoring or cutting balloons as medical devices are excluded. The Limus drug is an mTOR-inhibitor, preferably selected from sirolimus, everolimus, zotarolimus, biolimus and temsirolimus, most preferably sirolimus. Concerning preferred ways of carrying out this embodiment, the same applies as described above with respect to the combination of oxidation-insensitive drugs/drug preparations and lipophilic antioxidants.

Below, the invention is described by means of Examples.

EXAMPLE 1

Balloons for percutaneous transluminal coronary angioplasty type F were coated either with paclitaxel alone or combined with iopromide (iodinated contrast agent according to WO 02/076509), or butylated hydroxytoluene (BHT) or nordihydroguajaretic acid. Coated balloons were tested in respect of paclitaxel loss during the passage through a hemostatic valve, a Medtronic Launcher JL 3.5 6F guiding catheter and in stirred blood (37° C.) for one minute. When admixed at sufficient concentration to the coating solution, lipophilic antioxidants improve the adhesion of paclitaxel.

| Coating solution | Labeling | Loss on the way to the lesion % of dose |
|---|---|---|
| No additive: acetone/ethanol/H$_2$O | Control | 51 ± 15 |
| BHT 24% = 0.24 mg BHT/mg paclitaxel; acetone/ethanol/H$_2$O | D | 31 ± 16 |
| Nordihydroguaiaretic acid 35% = 0.35 mg/mg paclitaxel; acetone/ethanol/H$_2$O | E | 3.0 ± 4.9 |

EXAMPLE 2

Membranes type P were coated either with a water-soluble dye without resveratrol or combined with resveratrol. Coated membranes were tested in respect of dye loss during 5 min in stirred saline at 37° C. Resveratrol significantly improved the adhesion of the dye in spite of its solubility in water.

| Coating solution | Labeling | Loss of dye during 5 min in stirred saline % |
|---|---|---|
| Dye in solvent acetone/ethanol/H$_2$O | Control | 91 |
| Dye + Resveratrol 1.0 mg/ml acetone/ethanol/H$_2$O | R 1 | 1 |
| Dye + Resveratrol 5.2 mg/ml acetone/ethanol/H$_2$O | R 5 | 0 |

EXAMPLE 3

Balloons for percutaneous transluminal coronary angioplasty type F were coated in already folded condition either with paclitaxel without any additive or with various additives. Whereas it is known from example 1 that nordihydroguajaretic acid (NDGA) improves the adherence of paclitaxel to the balloon the impact on the distribution was unfavorable. Polyacrylic acid (molecular weight about 6000 D (Polysciences Inc., USA) and glycerol did neither improve adhesion nor significantly changed the distribution of the drug on the balloon. Combined with NDGA a favorable effect on the distribution of paclitaxel on the balloon was observed, particularly in respect of the penetration of the drug below the folds.

| Coating solution | Labeling | Distribution on balloons |
|---|---|---|
| Paclitaxel in acetone/tetrahydrofuran/H$_2$O | Control | Almost homogeneous distribution |
| 0.2 mg NDGA/mg paclitaxel in acetone/tetrahydrofuran/H$_2$O | NDGA | Spreading limited to directly accessible surface |
| 0.15 mg polyacrylic acid + 0.06 mg glycerol/mg paclitaxel in acetone/tetrahydrofuran/H$_2$O | Polymer | Almost homogeneous distribution |
| 0.2 mg NDGA + 0.15 mg polyacrylic acid + 0.06 mg glycerol/mg paclitaxel in acetone/tetrahydrofuran/H$_2$O | NDGA + Polymer | Perfectly homogeneous |

The invention claimed is:

1. A balloon catheter carrying at least on a portion of its surface polymer-free paclitaxel or a polymer-free paclitaxel preparation, and at least one lipophilic antioxidant at a ratio of 3-100% by weight of the at least one antioxidant in relation to 100% by weight of the paclitaxel, and the at least one lipophilic antioxidant is selected from the group consisting of nordihydroguaiaretic acid, resveratrol and propyl gallate, wherein scoring or cutting balloons as balloon catheters are excluded, and wherein said polymer-free paclitaxel or polymer-free paclitaxel preparation has an improved adherence to the balloon catheter without negative impact on the release of the polymer-free paclitaxel or polymer-free paclitaxel preparation.

2. The balloon catheter according to claim 1, wherein the device is an angioplasty balloon catheter for short lasting use during an interventional image guided procedure.

3. The balloon catheter according to claim 1, wherein the at least one lipophilic antioxidant is contained at a ratio of 5-100% by weight in relation to 100% by weight of the paclitaxel.

4. The balloon catheter according to claim 3, wherein the at least one lipophilic antioxidant is contained at a ratio of 10-100% by weight in relation to 100% by weight of the paclitaxel.

5. The balloon catheter according to claim 4, wherein the at least one lipophilic antioxidant is contained at a ratio of 20-100% by weight in relation to 100% by weight of the paclitaxel.

6. The balloon catheter according to claim 5, wherein the at least one lipophilic antioxidant is contained at a ratio of 50-100% by weight in relation to 100% by weight of the paclitaxel.

7. The balloon catheter according to claim 1, wherein the antioxidant load is up to 10 μg/mm$^2$ of coated device surface.

8. The balloon catheter according to claim 1, wherein the lipophilic antioxidant is nordihydroguaiaretic acid or resveratrol.

9. The balloon catheter according to claim 8, wherein the lipophilic antioxidant is resveratrol.

10. The balloon catheter according to claim 1, which has been sequentially coated polymer-free with paclitaxel and the at least one lipophilic antioxidant in a way that the paclitaxel and the antioxidant are not homogeneously mixed.

\* \* \* \* \*

UNITED STATES PATENT AND TRADEMARK OFFICE
CERTIFICATE OF CORRECTION

PATENT NO. : 9,974,888 B2  
APPLICATION NO. : 13/641941  
DATED : May 22, 2018  
INVENTOR(S) : Ulrich Speck and Madeleine Caroline Berg Page 1 of 1

It is certified that error appears in the above-identified patent and that said Letters Patent is hereby corrected as shown below:

On the Title Page

Title should read:
(54) IMPROVED FORMULATIONS FOR DRUG-COATED MEDICAL DEVICES

Signed and Sealed this
Tenth Day of July, 2018

Andrei Iancu
*Director of the United States Patent and Trademark Office*